US011381899B2

(12) United States Patent
Chou et al.

(10) Patent No.: US 11,381,899 B2
(45) Date of Patent: Jul. 5, 2022

(54) HEADPHONE CONTROL SYSTEM

(71) Applicants: FOXCONN (KUNSHAN) COMPUTER CONNECTOR CO., LTD., Kunshan (CN); FOXCONN INTERCONNECT TECHNOLOGY LIMITED, Grand Cayman (KY)

(72) Inventors: Wen-Kuei Chou, New Taipei (TW); Hui-Cheng Chen, New Taipei (TW); Hsu-Kuo Liang, New Taipei (TW)

(73) Assignees: FOXCONN (KUNSHAN) COMPUTER CONNECTOR CO., LTD., Kunshan (CN); FOXCONN INTERCONNECT TECHNOLOGY LIMITED, Grand Cayman (KY)

( * ) Notice: Subject to any disclaimer, the term of this patent is extended or adjusted under 35 U.S.C. 154(b) by 147 days.

(21) Appl. No.: 16/874,603

(22) Filed: May 14, 2020

(65) Prior Publication Data

US 2020/0366983 A1    Nov. 19, 2020

(30) Foreign Application Priority Data

May 14, 2019  (CN) .......................... 201910395686.1

(51) Int. Cl.
*H04R 1/10*   (2006.01)
*G05D 23/00*  (2006.01)
*H04S 7/00*   (2006.01)
*A61B 5/01*   (2006.01)

(52) U.S. Cl.
CPC ............. *H04R 1/1041* (2013.01); *A61B 5/01* (2013.01); *G05D 23/00* (2013.01); *H04S 7/304* (2013.01); *H04R 2460/03* (2013.01); *H04R 2460/07* (2013.01); *H04R 2499/10* (2013.01)

(58) Field of Classification Search
CPC .......................... H04R 1/1041; H04R 2460/03
See application file for complete search history.

(56) References Cited

U.S. PATENT DOCUMENTS

2018/0070166 A1*  3/2018  Howell ............... H04R 1/1016

FOREIGN PATENT DOCUMENTS

GN        104822103 B     10/2018
KR      20130065518 A  *   6/2013

OTHER PUBLICATIONS

English machine translation of KR 10-20130065518 (Lee et al., Earphone capable power control according temperature recognition and method for controlling thereof, published Jun. 2013) (Year: 2013).*

* cited by examiner

*Primary Examiner* — Mark Fischer
(74) *Attorney, Agent, or Firm* — Ming Chieh Chang; Wei Te Chung

(57) ABSTRACT

A headphone control system for use within a headphone includes a temperature sensor for detecting whether the circumference temperature of the headphone is relatively far from the human temperature implying the headphone is no longer worn by the user, and a gravity sensor for detecting whether the headphone is stationary implying that the headphone is not used for enabling a power saving mode, or is moving implying that the headphone is not yet unused for maintaining operation. The detection constantly is applied to the headphone disregarding whether the headphone is in an operation mode or a power saving mode so as to efficiently have the headphone operated in response to currently using or power-saved in response to non-using.

7 Claims, 2 Drawing Sheets

HEADPHONE CONTROL SYSTEM

BACKGROUND OF THE INVENTION

1. Field of the Invention

The present invention relates generally to a headphone control system, and particular to the headphone control system activating power saving.

2. Description of Related Arts

An operation of the Bluetooth headphone may be controllably adjusted either by the device to which the headphone is wirelessly connected, or by the button on the headphone. Such operation may include the volume adjustment and/or the power on and off. Sometimes, the user may temporarily take off the headphone for either resting or being interrupted by something, a manual power-off action may be bothersome.

Therefore, it is desired to have the headphone equipped with a smart control system which may efficiently verify whether the headphone is currently requisitely used by someone for maintaining operation, or otherwise switching to a power saving mode.

SUMMARY OF THE INVENTION

To achieve the above object, a headphone control system for use within a headphone includes a temperature sensor for detecting whether the circumference temperature of the headphone is relatively far from the human temperature implying the headphone is no longer worn by the user, and a gravity sensor for detecting whether the headphone is stationary implying that the headphone is not used for enabling a power saving mode, or is moving implying that the headphone is not yet unused for maintaining operation. The detection constantly is applied to the headphone disregarding whether the headphone is in an operation mode or a power saving mode so as to efficiently have the headphone operated in response to currently using or power-saved in response to non-using.

Other advantages and novel features of the invention will become more apparent from the following detailed description of the present embodiment when taken in conjunction with the accompanying drawings.

DETAILED DESCRIPTION OF THE PREFERRED EMBODIMENT

Figure 1:
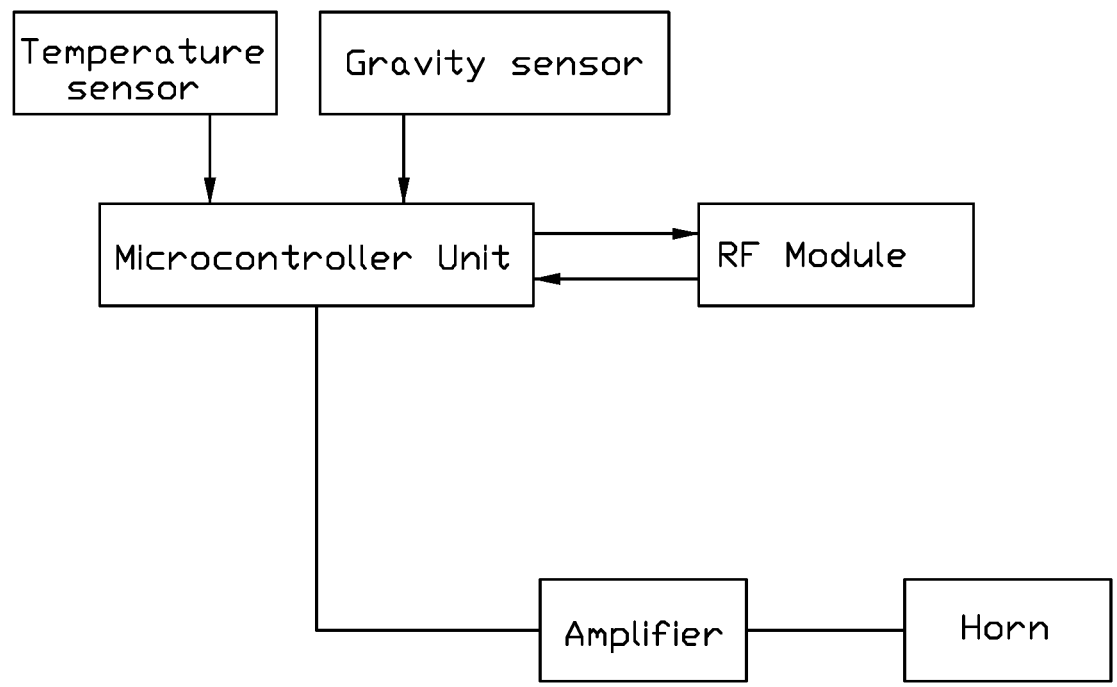
FIG. 1 is a diagram showing the control system used in the headphone.
Figure 2:
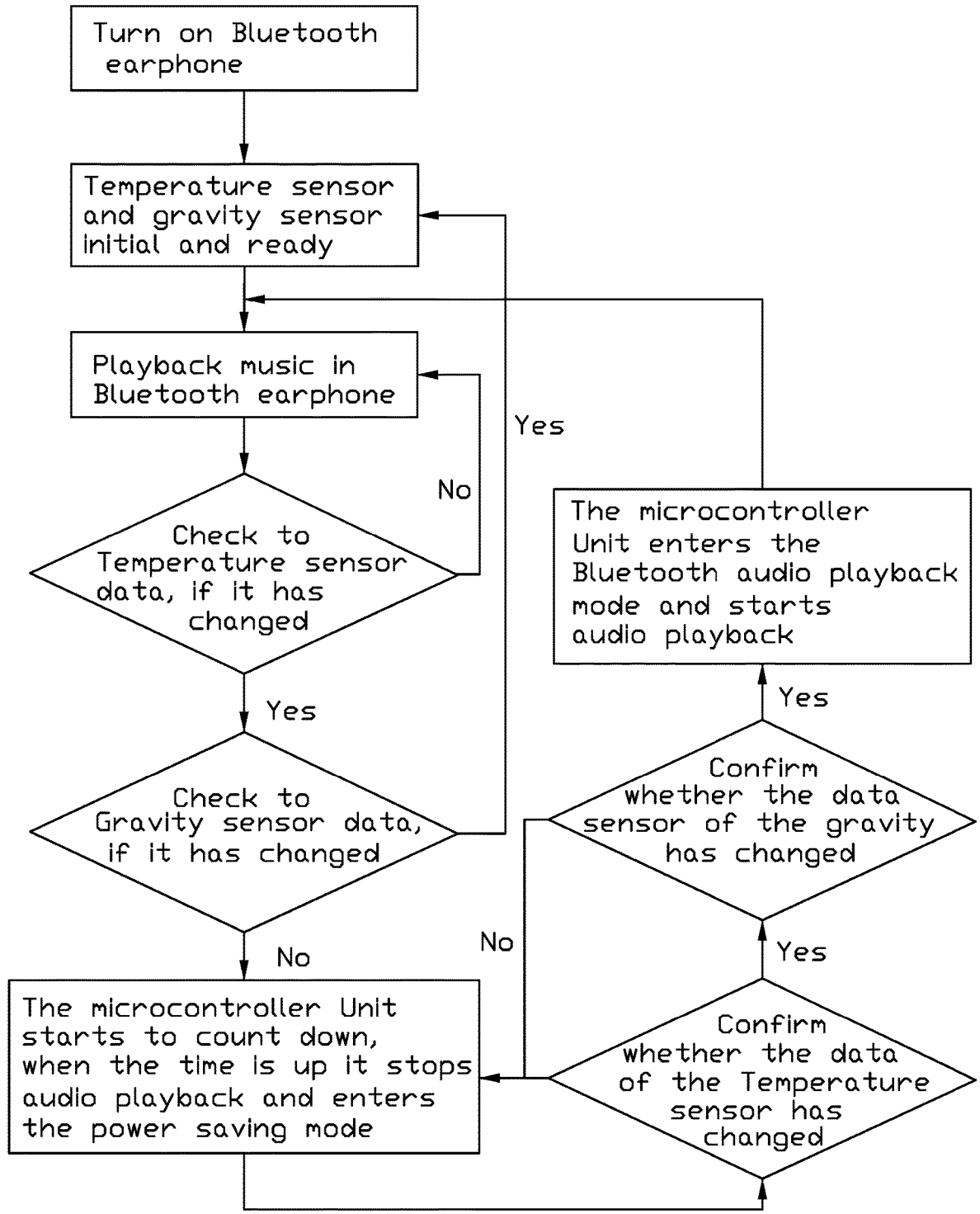
FIG. 2 is a flow chart of operation of the control system of FIG. 1.

Referring to FIGS. 1-2, the headphone or earphone is of a Bluetooth type, and the control system is built within the headphone. Notably, the Bluetooth headphone includes an amplifier, an RF (Radio Frequency) module, and a speaker/horn. The control system includes a temperature sensor, a gravity sensor and a microcontroller unit. The RF module sends the data of the device to the microcontroller so as to decide the status of the headphone.

When the headphone is powered on, the temperature sensor constantly detects the circumference temperature of the headphone. The headphone maintains the operation or playback status when the temperature is unchanged and/or corresponding to the human temperature in a regular manner. When the temperature is changed and/or not corresponding to the human temperature in an irregular condition, the gravity sensor further detects whether the headphone is stationary or not. Under such a temperature irregular condition, when the headphone is further detected to be stationary, the headphone is switched to a power saving mode. Understandably, this situation may be referred to the user taking off the headphone temporarily, and the sound derived from the device may be temporarily suspended. Notably, such a power saving mode may be triggered in 30 seconds rather than instantly, as the operation of the screen power saving mode used in the computer or the mobile phone. In opposite, when the headphone is further detected to be moving under the aforementioned temperature irregular condition, the headphone is set/switched to in the operation mode. Understandably, this situation may be referred to the user putting on the headphone. In conclusion, the user does not need to manually control the sound or the power of the headphone when he takes off the headphone or puts on the headphone again advantageously. FIG. 2 shows how the control system stops the audio playback to have the headphone is in a power saving mode when the headphone is playing the sound in an operation mode, and restarts the audio playback to have the headphone back to an operation mode when the headphone is in a power saving mode. Clearly, such stopping and restarting results in an automatic circular operation without requiring manual operation advantageously.

Although the present invention has been described with reference to particular embodiments, it is not to be construed as being limited thereto. Various alterations and modifications can be made to the embodiments without in any way departing from the scope or spirit of the present invention as defined in the appended claims.

What is claimed is:

1. A control system of a wireless headphone comprising:
   a microcontroller unit;
   an amplifier and a speaker electrically connected to the microcontroller unit; and
   a temperature sensor and a gravity sensor electrically connected to the microcontroller unit; wherein
   when the temperature sensor verifies a circumference temperature of the headphone corresponds to the human temperature, the headphone maintains in a playback status; and
   when the temperature sensor verifies the circumference temperature of the headphone does not correspond to the human temperature, the headphone is switched to a power saving mode if the gravity sensor further verifies the headphone is stationary.

2. The control system as claimed in claim 1, further including an RF (Radio Frequency) module electrically connected to the microcontroller unit.

3. A method of controlling an operation of a headphone comprising steps of:
   providing a microcontroller unit;
   providing a temperature sensor and a gravity sensor electrically connected to the microcontroller unit;
   verifying a circumference temperature of the headphone via said temperature sensor to maintain a playback status of the headphone if said circumference temperature of the headphone corresponds to a human temperature; and further verifying movement of the headphone via said gravity sensor if said circumference temperature of the headphone does not correspond to the human temperature.

4. The method as claimed in claim 3, wherein the headphone is switched to a power saving mode if the headphone is not moved.

5. The method as claimed in claim 4, wherein switching to the power saving mode is activated with a time delay not less than 10 seconds.

6. The method as claimed in claim 3, wherein the headphone is switched to a playback mode if the headphone is moving.

7. A control system of a wireless headphone, comprising:
a microcontroller unit;
an amplifier and a speaker electrically connected to the microcontroller unit; and
a temperature sensor and a gravity sensor electrically connected to the microcontroller unit; wherein
when the temperature sensor verifies a circumference temperature of the headphone corresponds to the human temperature, the headphone maintains in a playback status; and
when the temperature sensor verifies the circumference temperature of the headphone does not correspond to the human temperature, the headphone is switched to the playback status if the gravity sensor further verifies the headphone is moving.

* * * * *